(12) United States Patent
Vaidyanathan

(10) Patent No.: US 11,744,971 B2
(45) Date of Patent: Sep. 5, 2023

(54) EXPANDABLE ENDOTRACHEAL TUBE

(71) Applicant: Northwestern University, Evanston, IL (US)

(72) Inventor: Mahesh Vaidyanathan, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/512,434

(22) Filed: Oct. 27, 2021

(65) Prior Publication Data
US 2022/0047832 A1 Feb. 17, 2022

Related U.S. Application Data

(63) Continuation of application No. PCT/US2021/024840, filed on Mar. 30, 2021.

(60) Provisional application No. 63/001,868, filed on Mar. 30, 2020.

(51) Int. Cl.
*A61M 16/04* (2006.01)
*A61M 16/00* (2006.01)

(52) U.S. Cl.
CPC .... *A61M 16/0434* (2013.01); *A61M 16/0003* (2014.02); *A61M 2207/00* (2013.01); *A61M 2230/432* (2013.01); *A61M 2230/50* (2013.01)

(58) Field of Classification Search
CPC ............ A61M 16/044; A61M 2205/42; A61M 16/0434; A61M 16/0445; A61M 16/0436; A61M 16/0003; A61M 16/0443–0459; A61M 25/0021–0023; A61M 2025/0024–0025
See application file for complete search history.

(56) References Cited

U.S. PATENT DOCUMENTS

| | | | | |
|---|---|---|---|---|
| 4,016,885 A * | 4/1977 | Bruner | ................. | A61M 16/044 604/100.01 |
| 4,501,273 A * | 2/1985 | McGinnis | ........... | A61M 16/044 128/207.15 |
| 5,638,813 A * | 6/1997 | Augustine | ............. | A61M 16/04 128/207.15 |
| 6,553,993 B2 | 4/2003 | Toti et al. | | |
| 6,562,064 B1 * | 5/2003 | deBeer | ....................... | A61F 2/95 606/108 |
| 8,196,584 B2 * | 6/2012 | Maguire | ........... | A61M 16/0445 128/207.14 |

(Continued)

OTHER PUBLICATIONS

The International Search Report and the Written Opinion dated Aug. 12, 2021 for International patent application No. PCT/US21/24840; pp. 1-13.

*Primary Examiner* — Joseph D. Boecker
*Assistant Examiner* — Thomas W Greig
(74) *Attorney, Agent, or Firm* — Bell & Manning, LLC

(57) ABSTRACT

An expandable endotracheal tube includes a shaft that has an airway. The expandable endotracheal tube also includes an expandable segment mounted to a distal end of the shaft. The expandable segment includes an expandable membrane and a constant force spring positioned within the expandable membrane. The constant force spring has a compressed configuration to allow for placement of the expandable endotracheal tube within a patient and an expanded configuration in which the expandable membrane forms a seal with a trachea of the patient to enable positive pressure ventilation.

16 Claims, 15 Drawing Sheets

(56) References Cited

U.S. PATENT DOCUMENTS

| | | |
|---|---|---|
| 8,807,136 B2 | 8/2014 | O'Neil et al. |
| 9,364,628 B2 * | 6/2016 | Hwang .............. A61M 16/0434 |
| 9,636,116 B2 * | 5/2017 | Rudakov .......... A61B 17/12036 |
| 2005/0183729 A1 * | 8/2005 | Fischer ............. A61M 16/0429 |
| | | 128/207.14 |
| 2008/0078399 A1 * | 4/2008 | O'Neil .............. A61M 16/0443 |
| | | 128/207.14 |
| 2008/0200776 A1 * | 8/2008 | Schermeier ....... A61M 16/1065 |
| | | 600/301 |
| 2011/0048427 A1 | 3/2011 | Zachar |
| 2012/0220845 A1 | 8/2012 | Campbell |
| 2014/0378766 A1 | 12/2014 | Lo |
| 2015/0151063 A1 | 6/2015 | Hoftman et al. |
| 2016/0038008 A1 | 2/2016 | Molnar |
| 2020/0030559 A1 * | 1/2020 | Avniel .............. A61M 16/0434 |

\* cited by examiner

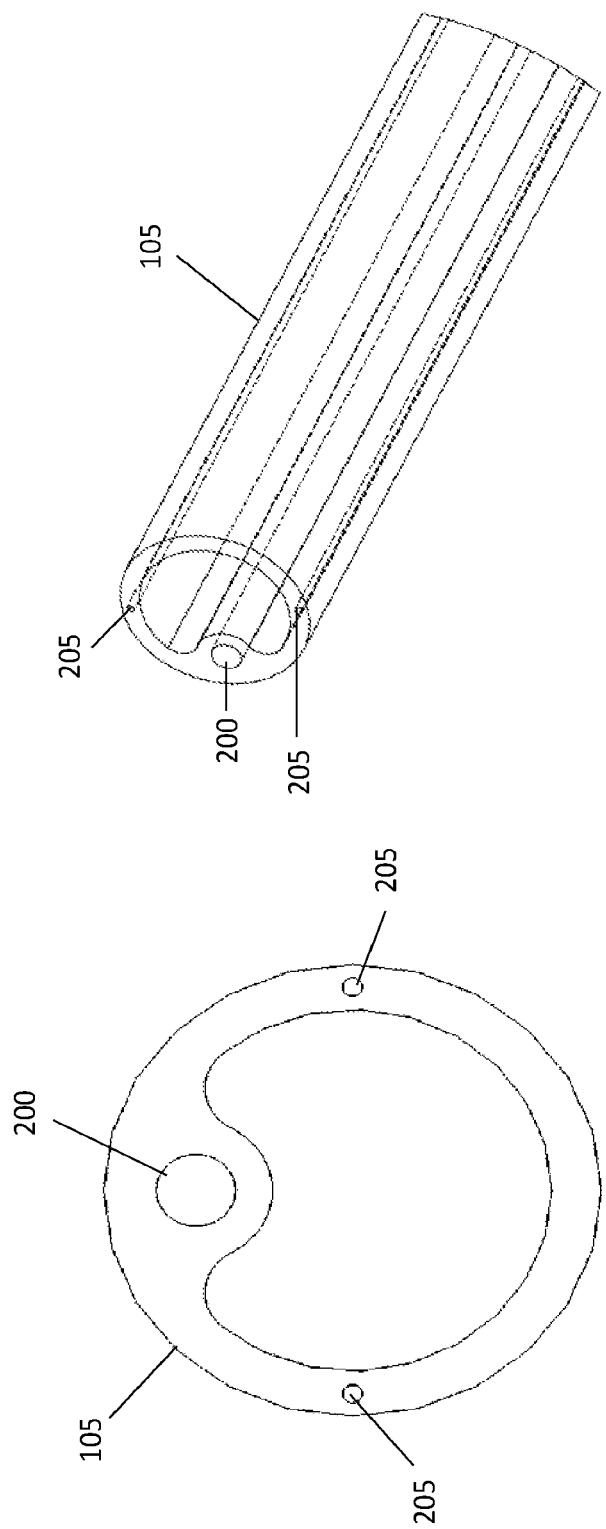

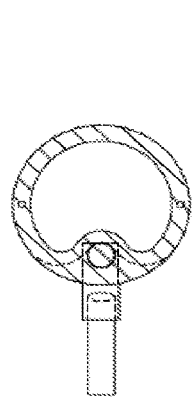
Fig. 4C
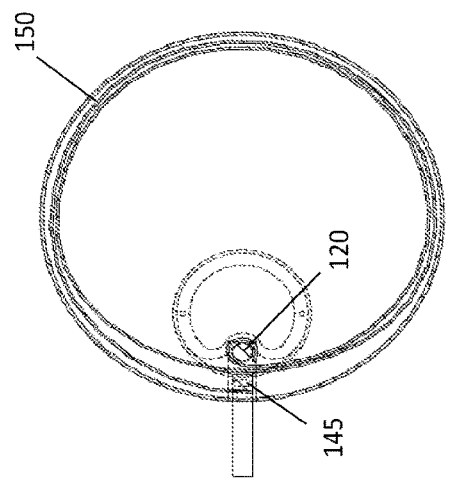
Fig. 4D
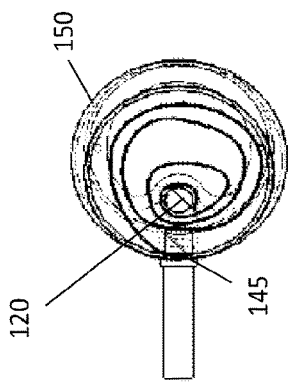
Fig. 4E
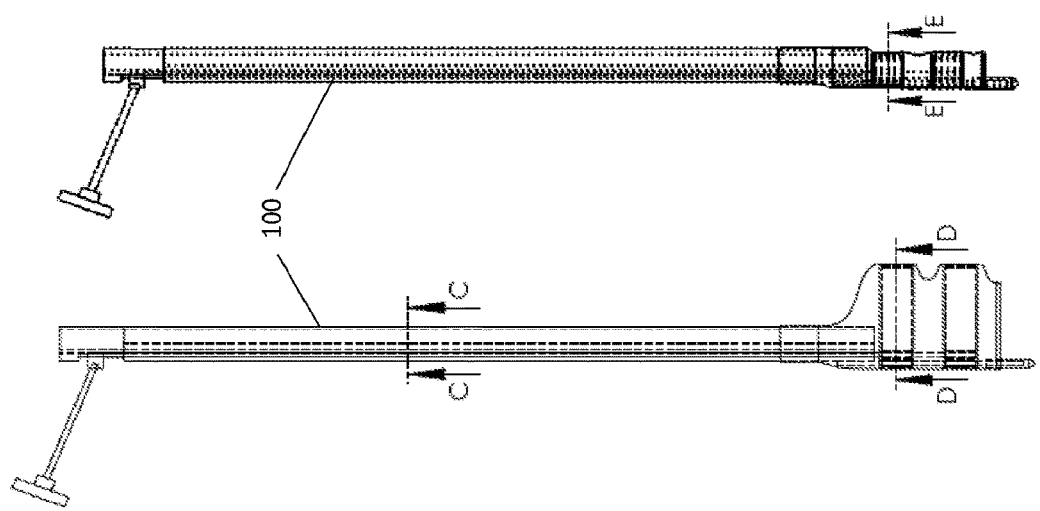
Fig. 4A
Fig. 4B

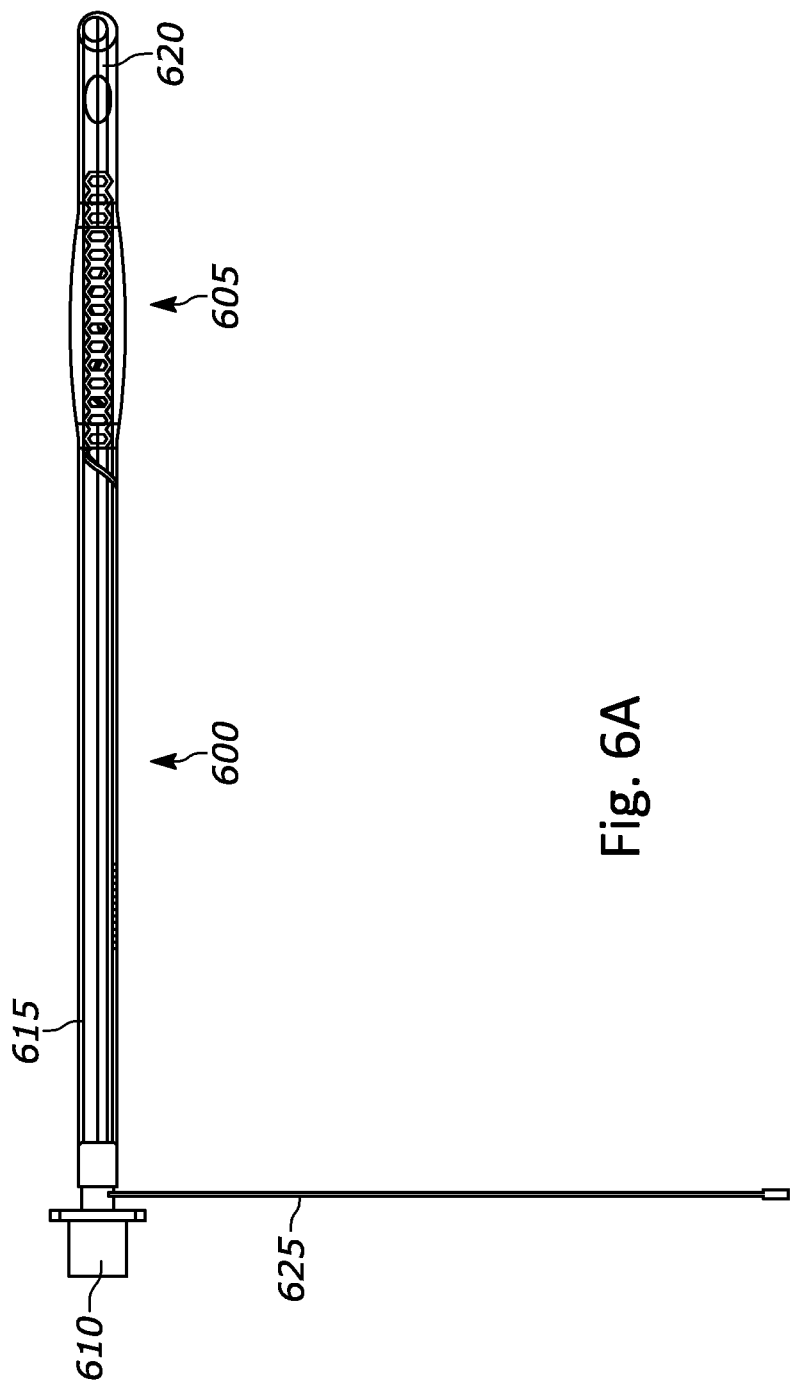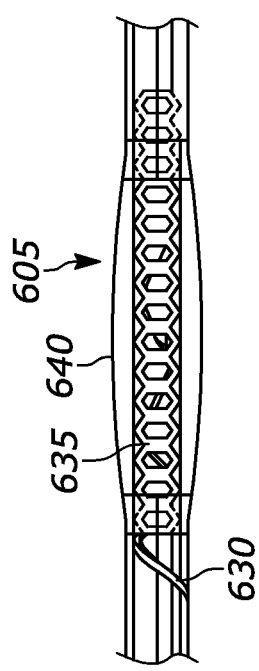
Fig. 6A
Fig. 6B

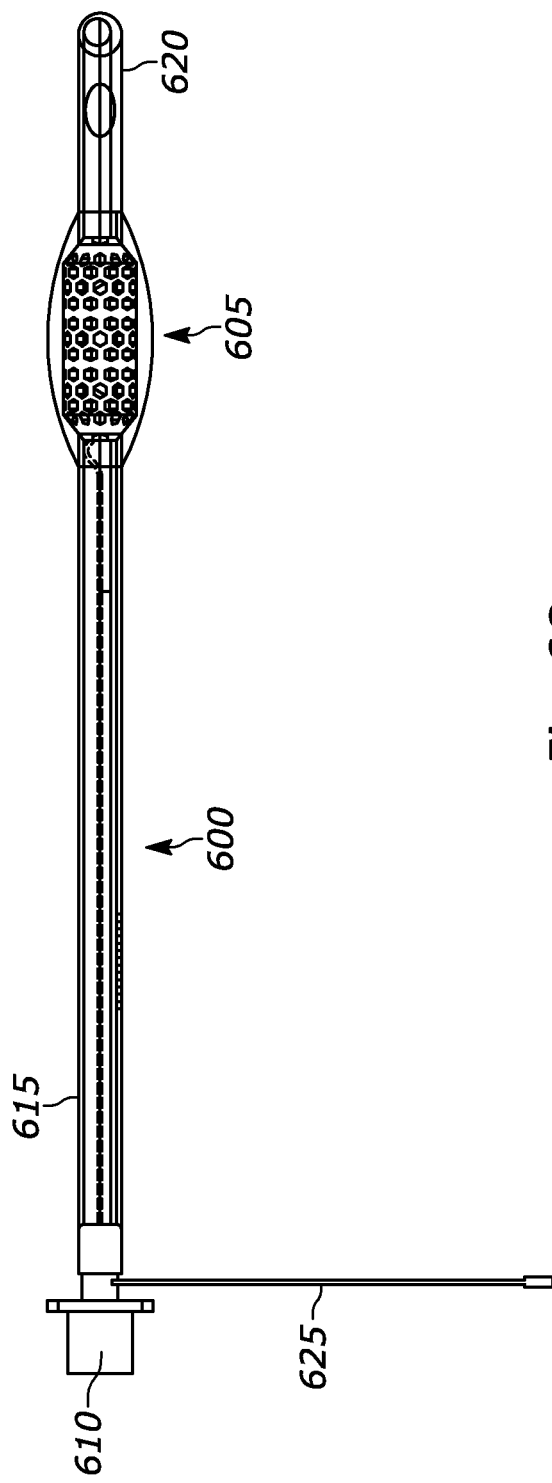
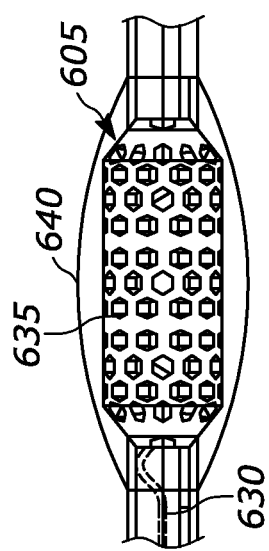
Fig. 6C
Fig. 6D

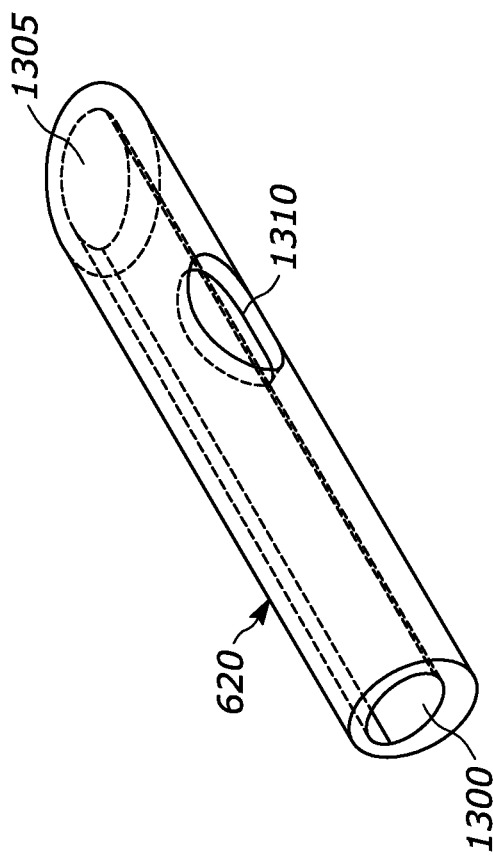
Fig. 13A
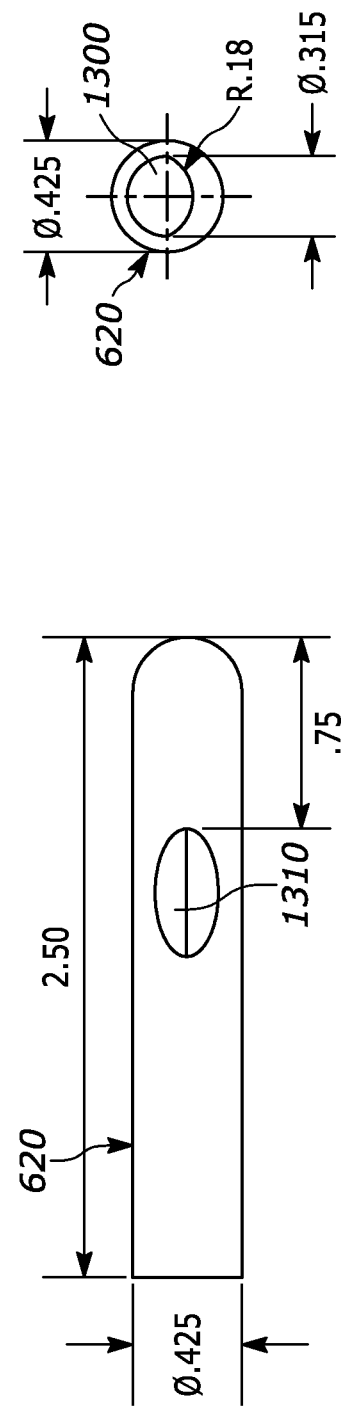
Fig. 13C
Fig. 13B

EXPANDABLE ENDOTRACHEAL TUBE

CROSS-REFERENCE TO RELATED APPLICATION

The present application is a continuation application of International Application No. PCT/US21/24840, filed on Mar. 30, 2021, which claims priority to U.S. Provisional Patent Application No. 63/001,868 filed on Mar. 30, 2020, the entire disclosures of which are incorporated by reference herein.

BACKGROUND

An endotracheal tube is a flexible tube that is used to help a patient breathe. The tube is placed through the mouth of the patient and into the trachea. The endotracheal tube can then be connected to a ventilator that is used to deliver air to the lungs of the patient. Endotracheal tubes are used during medical procedures in which the patient is given a general anesthetic, to help a patient breathe after experiencing trauma, to help a patient breathe during a severe illness, to help remove an aspirated foreign body, to prevent contents of the stomach from entering the airway, etc.

SUMMARY

An illustrative expandable endotracheal tube includes a shaft that has an airway. The expandable endotracheal tube also includes an expandable segment mounted to a distal end of the shaft. The expandable segment includes an expandable membrane and a constant force spring positioned within the expandable membrane. The constant force spring has a compressed configuration to allow for placement of the expandable endotracheal tube within a patient and an expanded configuration in which the expandable membrane forms a seal with a trachea of the patient to enable positive pressure ventilation.

An illustrative method of making an expandable endotracheal tube includes forming a shaft that has a proximal end and a distal end, where the shaft has an airway that runs longitudinally within the shaft. The method also includes mounting a fixed rod to a distal end of the shaft. The method also includes mounting an expandable segment to the distal end of the shaft. Mounting the expandable segment includes mounting a constant force spring such that a first end of the constant force spring is mounted to the fixed rod. The constant force spring has a compressed configuration to allow for placement of the expandable endotracheal tube within a patient and an expanded configuration in which the expandable segment forms a seal with a trachea of the patient to enable positive pressure ventilation. The method further incudes mounting an expandable membrane to the shaft such that the expandable membrane surrounds the constant force spring.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 2A is an end view of the tube in accordance with an illustrative embodiment.

FIG. 2B is a partial transparent view of the tube in accordance with an illustrative embodiment.

FIG. 4A depicts the expandable endotracheal tube in an expanded configuration with section lines C:C and D:D in accordance with an illustrative embodiment.

FIG. 4B depicts the expandable endotracheal tube in a compressed configuration with section line E:E in accordance with an illustrative embodiment.

FIG. 4C depicts a cross-section view of the expandable endotracheal tube along section line C:C in accordance with an illustrative embodiment.

FIG. 4D depicts a cross-section view of the expandable endotracheal tube along section line D:D in accordance with an illustrative embodiment.

FIG. 4E depicts a cross-section view of the expandable endotracheal tube along section line E:E in accordance with an illustrative embodiment.

FIG. 6A is a side view of an expandable endotracheal tube in a compressed (or unexpanded) state in accordance with an illustrative embodiment.

FIG. 6B is a close-up sectional view of an expandable segment of the expandable endotracheal tube in the compressed state in accordance with an illustrative embodiment.

FIG. 6C is a side view of the expandable endotracheal tube in an expanded state in accordance with an illustrative embodiment.

FIG. 6D is a close-up sectional view of the expandable segment of the expandable endotracheal tube in the expanded state in accordance with an illustrative embodiment.

FIG. 10C is a sectional view of a proximal end of the expandable helix in accordance with an illustrative embodiment.

FIG. 13A is a perspective view of the tube tip in accordance with an illustrative embodiment.

FIG. 13B is a side view of the tube tip in accordance with an illustrative embodiment.

FIG. 13C is an end view of the tube tip in accordance with an illustrative embodiment.

DETAILED DESCRIPTION

Figure 1A:
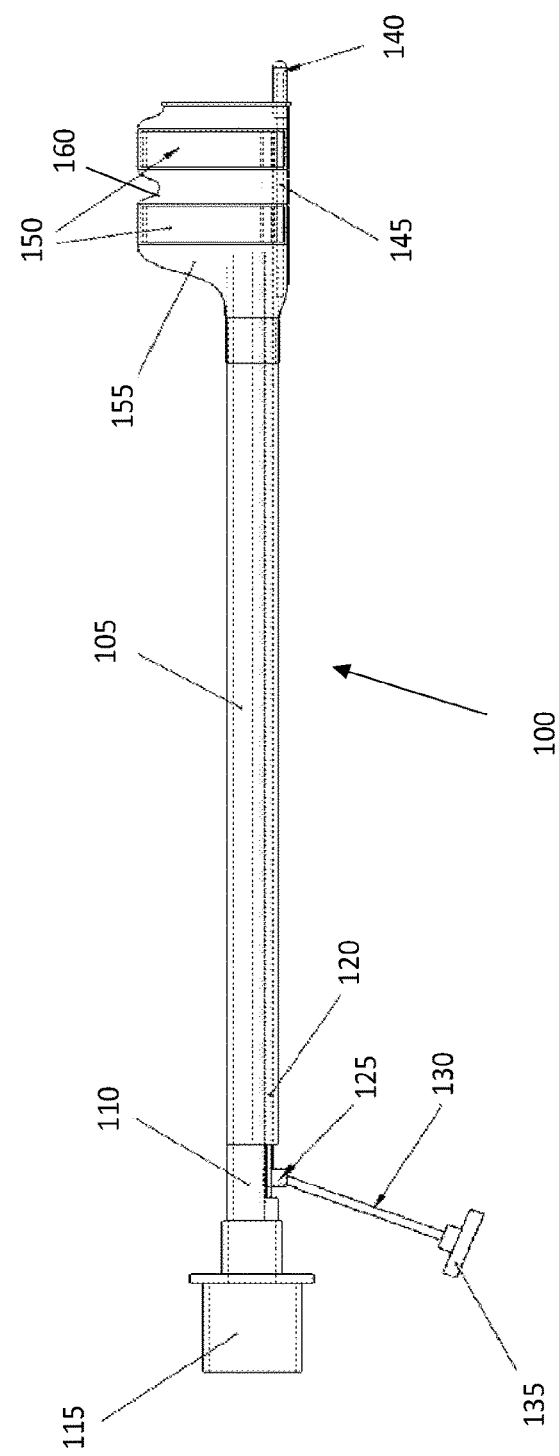
FIG. 1A is a side view of an expandable endotracheal tube in an expanded state in accordance with an illustrative embodiment.

Traditional endotracheal tubes are manufactured in multiple sizes to accommodate patients of various sizes. As a result, hospitals and other medical centers and emergency medical technicians (EMTs) that use endotracheal tubes have to keep numerous different tubes in stock, which adds significant cost to operations. Having a large number of different tubes also requires the physician to select the correct size for a given patient, which can result in lost time during an emergency. Selecting tubes on a patient-by-patient basis also introduces the potential for human error in making the size selection. An improperly sized endotracheal tube may result in difficulty intubating the patient or difficulty ventilating the patient in some circumstances. If the tube is left in place with the cuff expanded for an extended period of time it can also potentially cause injury to the patient in the form of subglottic stenosis. Additionally, traditional endotracheal tubes require use of a separate rigid stylet during intubation and a syringe to inflate a distally located balloon that is designed to allow for positive pressure ventilation. The stylets and syringes are additional components that medical centers, EMTs, etc. are required to keep in stock and have readily available for every intubation.

Described herein are expandable endotracheal tubes that are designed to fit any patient, regardless of size. The proposed endotracheal tubes also function without the use of a separate stylet or a separate syringe. As a result, the proposed expandable endotracheal tubes remove the need for medical centers to stock multiple tube sizes, associated stylets, or associated syringes. The expandable endotracheal tubes also eliminate the decision-making process to determine the appropriate size tube for a patient. Additionally, the proposed tubes remove the need to inflate a balloon with a syringe, and decrease the likelihood that the patient will experience soft tissue injury due to pressure necrosis. As described herein, the proposed tubes are configured to expand as large as possible without causing injury to the patient. This full expansion within the patient prevents leakage and improves ventilation as compared to traditional endotracheal tubes. The expandable endotracheal tubes can be used in general surgery cases, on intubated intensive care unit (ICU) patients, on patients requiring emergency room intubation, on patients requiring emergency intubation on a hospital floor, on patients requiring intubation by an EMT, and any other procedures or situations in which a patient needs intubation.

In an illustrative embodiment, the proposed expandable endotracheal tubes have two possible conformations. In an intubating conformation, an expandable segment of the tube is in a compressed state such that a rigid or semi-rigid tube tip (or bougie) functions as a stylet. For example, the tube tip can be designed to be stiff and to be slightly curved in the anterior direction. In the ventilation conformation, the expandable segment of the tube is in an expanded state such that the distal end of the proposed tube acts as a continuation of its proximal end, which allows the air from the ventilator to reach the patient without obstruction. The proposed endotracheal tubes are described in detail below with reference to the figures.

Figure 1B:
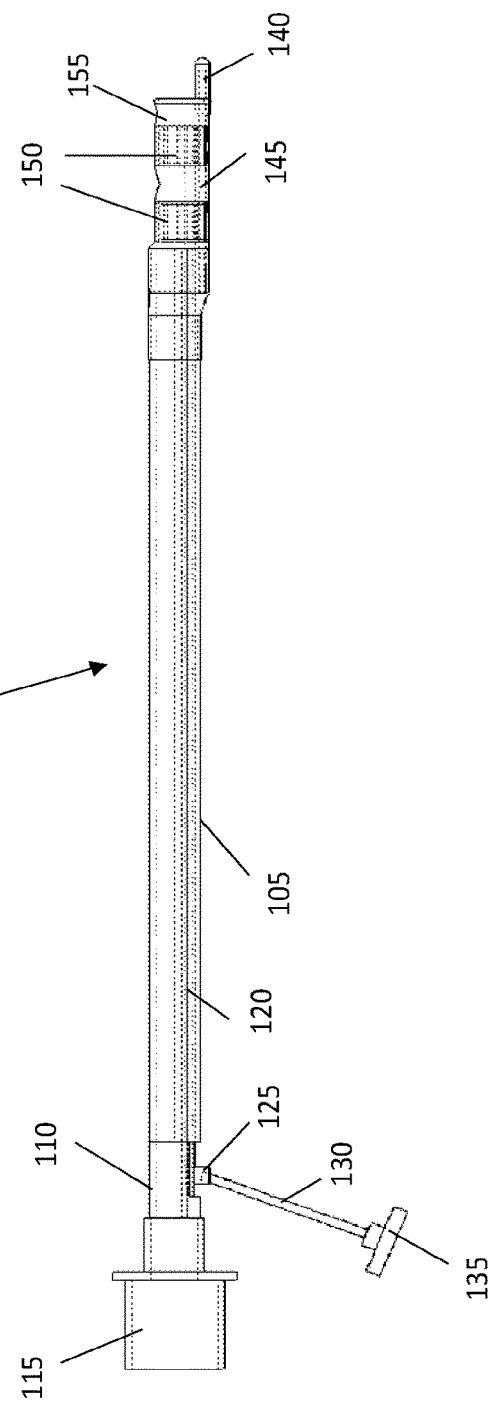
FIG. 1B is a side view of the expandable endotracheal tube in a compressed state in accordance with an illustrative embodiment.

FIG. 1A is a side view of an expandable endotracheal tube 100 in an expanded state in accordance with an illustrative embodiment. FIG. 1B is a side of the expandable endotracheal tube 100 in a compressed state in accordance with an illustrative embodiment. The expandable endotracheal tube 100 includes a shaft (or tube) 105. The shaft 105 can be sized to fit a wide variety of patients. For example, in at least some embodiments, the proposed expandable endotracheal tube 100 can be used for both pediatric and small adult patients. As discussed, the ability to use a single device for such a wide array of patients significantly reduces the number of devices that need to be stocked, and helps ensure that medical facilities will always have the correct size in stock. In one embodiment, an overall diameter of the shaft can be 6-10 millimeters (mm). Alternatively, the diameter can be less than 6 mm or greater than 10 mm for certain patient sizes or situations. The shaft can be made from any biocompatible material such as silicon, polyethylene, etc. A shaft adapter 110 is mounted to a proximal end of the shaft 105 and is designed to receive an airway adapter 115, which can be used for attachment of the expandable endotracheal tube 100 to a breathing circuit and ventilator. The shaft adapter 110 and the airway adapter 115 can be made from polyethylene in one embodiment. Alternatively, a different material may be used. The shaft adapter 110 and the airway adapter 115 can be mounted to the shaft 105 and/or to one another via a friction fit, adhesive, etc. Mounted within the shaft 105 is a control rod 120 that is used expand and compress an expandable segment of the system, as described in more detail below.

In an illustrative embodiment, in addition to supporting the control rod 120, the shaft 105 also allows for the use of sensors. FIG. 2A is an end view of the shaft 105 in accordance with an illustrative embodiment. FIG. 2B is a partial transparent view of the shaft 105 in accordance with an illustrative embodiment. As shown, formed in the body of the shaft 105 is a control rod port 200 that is sized to receive the control rod 120 such that the control rod 120 is able to rotate within the control rod port 200. The control rod port 200 extends the entire length of the shaft 105 such that the control rod 120 extends into an expandable segment of the expandable endotracheal tube 100, as discussed in detail below. Additionally, the shaft 105 includes sensor ports 205 formed in the body of the shaft 105 and that extend the entire length of the shaft. As shown, the body portion of the shaft 105 that includes the control rod port 200 is wider than the body portion of the shaft 105 that includes the sensor ports 205. The sensor ports allow one or more sensors to be placed into the patient's airway (or beyond) for patient monitoring. In one embodiment, the sensors can be attached to wires which are placed into the sensor ports 205 and used to deliver the sensors through the shaft 105 and into the patient's airway.

In an illustrative embodiment, the sensors used with the expandable endotracheal tube 100 can include one or more temperature sensors and/or one or more carbon dioxide ($CO_2$) sensors. The one or more temperature sensors are used to monitor an internal temperature of the patient. The one or more carbon dioxide sensors are used to identify $CO_2$ exhaled by the patient to help ensure that the tube is initially placed in the trachea and not in the esophagus. Additionally, this sensor can be used to monitor both inhaled ($FiCO_2$) and exhaled ($ETCO_2$) $CO_2$, which in traditional systems is currently managed by additional monitors in the OR and ICUs. The sensor(s) can be mounted in the patient by way of the sensor ports 205 within the shaft 105. Data sensed by the sensor(s) can be transmitted to a computing device (e.g., smartphone, tablet, laptop, etc.) via wired or wireless communication, and a user can monitor the data through the computing device. The embodiment of FIG. 2 depicts two sensor ports. In alternative embodiment embodiments, fewer or additional sensor ports may be used, such as one sensor port, three sensor ports, etc.

Referring back to FIG. 1, the control rod 120 is rotated in a first direction (e.g., clockwise) to expand the expandable segment of the system, and in a second opposite direction (e.g., counterclockwise) to compress the expandable segment. Rotation of the control rod 120 is facilitated by a control system that includes a joint 125, an angled rod 130, and a handle 135. A user can manipulate the handle 135 of the control system to rotate the control rod 120 in either direction. The handle 135 is depicted as a wheel in FIG. 1, however other configurations of the handle may be used in alternative embodiments. In other embodiments, the handle 135 may be replaced by a spring loaded button or lever that acts to rotate the control rod 120 via ratcheting. The angled rod 130 is angled away from the proximal end of the shaft 105 such that the handle 135 can be manipulated by the user without interference from the shaft 105, shaft adapter 110, and airway adapter 115. In an illustrative embodiment, the angled rod 130 is positioned at an angle between 20° and 90° relative to the shaft 105. Alternatively, a different angle may be used. In an alternative embodiment, the angled rod 130 and joint 125 may not be used, and the handle 135 can be mounted directly onto the control rod 120.

Figure 3C:
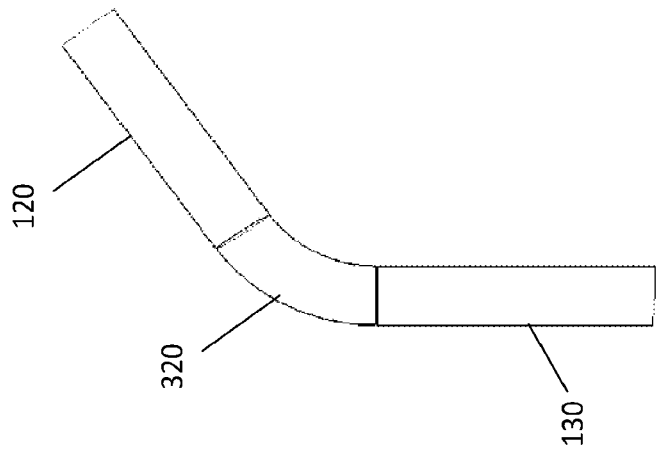
FIG. 3C depicts a joint in accordance with a third illustrative embodiment.

In the depicted embodiment, the angled rod 130 rotates in unison with the handle 135, and the rotation is imparted onto the control rod 120 by way of the joint 125. The joint can include gears to provide rotation in an illustrative embodiment. FIG. 3A depicts a joint in accordance with a first illustrative embodiment. As shown, the joint includes a first gear 300 mounted to the angled rod 130 and a second gear 305 mounted to the control rod 120 in accordance with an illustrative embodiment. Rotation of the handle 135 causes rotation of the angled rod 130 and the first gear 300 mounted thereto. This rotation is transferred from the first gear 300 to the second gear 305, which causes rotation of the second gear 305 and the control rod 120 to which the second gear 305 is mounted.

Figure 3B:
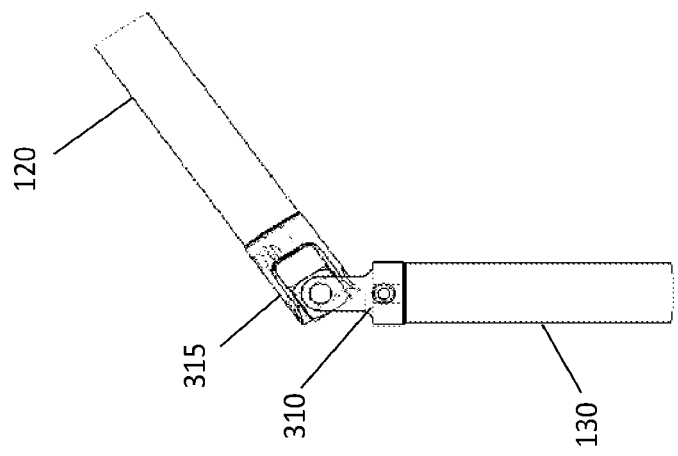
FIG. 3B depicts a joint in accordance with a second illustrative embodiment.
Figure 3A:
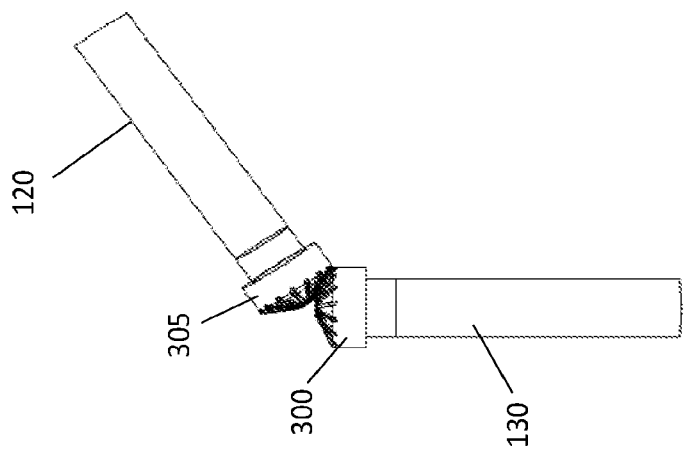
FIG. 3A depicts a joint in accordance with a first illustrative embodiment.

FIG. 3B depicts a joint in accordance with a second illustrative embodiment. As shown, the joint includes a first u-bolt 310 mounted to the angled rod 130 and a second u-bolt 315 mounted to the control rod 120 in accordance with an illustrative embodiment. Rotation of the handle 135 causes rotation of the angled rod 130 and the first u-bolt 310 mounted thereto. This rotation is transferred from the first u-bolt 310 to the second u-bolt 315, which causes rotation of the second u-bolt 315 and the control rod 120 to which the second u-bolt 315 is mounted. FIG. 3C depicts a joint in accordance with a third illustrative embodiment. As shown, the joint of FIG. 3C is a softened flexible joint 320 mounted between the angled rod 130 and the control rod 120 in accordance with an illustrative embodiment. Rotation of the handle 135 causes rotation of the angled rod 130 and the flexible joint 320 mounted thereto. This rotation is transferred from the flexible joint 320 to the control rod 120 to which the other end of the flexible joint 320 is mounted.

Referring back to FIGS. 1A and 1B, the expandable segment of the expandable endotracheal tube 100 is positioned at the distal end of the shaft 105. The expandable segment includes a fixed rod 145 that is stationary. The fixed rod 145 is mounted to the shaft 105 using an adhesive, a male/female friction fit connection, etc. Constant force springs 150 (e.g., Tensator springs) are included in the expandable segment to provide the compression and expansion. The constant force springs 150 are formed from a coiled strip of material that has a first end and a second end. The constant force springs 150 can be formed from a nitinol sheet in one embodiment, and the thickness of the sheet can be less than 0.1 mm. Alternatively, a different material and/or material thickness may be used.

A first end of each of the constant force springs 150 is mounted to the fixed rod 145 and a second end of each of the constant force springs 150 is mounted to the control rod 120. As a result, rotation of the control rod 120 causes expansion or compression of the constant force springs 150, depending on the direction of rotation. The embodiment of FIG. 1 depicts 2 constant force springs. However, it is to be understood that in alternative embodiments, the system may include a single constant force spring, three constant force springs, four constant force springs, etc. The expandable segment also includes a bougie 140 that takes the place of a stylet and is used to guide the expandable endotracheal tube 100 into the patient. The bougie 140 can be made from rubber or any other rigid or semi-rigid biocompatible material. The bougie 140 can be mounted to the shaft 105, the fixed rod 145, and/or the constant force springs 150, depending on the embodiment.

An expandable membrane 155 is mounted to the distal end of the shaft 105 using an adhesive or other mounting technique, and surrounds the constant force springs 150 and the fixed rod 145. The expandable membrane 155 can be made from rubber or another expandable material. The expandable membrane 155 is the primary point of contact of the expandable endotracheal tube 100 to the patient. In one embodiment, the expandable membrane compresses down to 6 mm or smaller and expands out to 30 mm or larger to accommodate a wide range of patients. Alternatively, different dimensions may be used. As shown, spacing between the constant force springs 150 results in a groove 160 formed in the expandable membrane 155. This groove 160 is designed to mate with a cartilage ring within the patient's airway, which helps create a seal between the expandable endotracheal tube and the trachea and allow for positive pressure air flow within the system. In alternative embodiments, additional grooves may be formed by including additional constant force springs within the expandable membrane 155. For example, three constant force springs can be used to provide two grooves in the expandable membrane, four constant force springs can be used to provide three grooves in the expandable membrane, etc.

FIG. 4A depicts the expandable endotracheal tube 100 in an expanded configuration with section lines C:C and D:D in accordance with an illustrative embodiment. FIG. 4B depicts the expandable endotracheal tube 100 in a compressed configuration with section line E:E in accordance with an illustrative embodiment. FIG. 4C depicts a cross-section view of the expandable endotracheal tube 100 along section line C:C in accordance with an illustrative embodiment. FIG. 4D depicts a cross-section view of the expandable endotracheal tube 100 along section line D:D in accordance with an illustrative embodiment. FIG. 4E depicts a cross-section view of the expandable endotracheal tube 100 along section line E:E in accordance with an illustrative embodiment. As shown in FIGS. 4D and 4E, a first end of the constant force spring 150 is mounted to the control rod 120 and a second end of the constant force spring is mounted to the fixed rod 145 such that rotation of the control rod 120 adjusts the overall size (diameter) of the constant force spring 150.

Figure 5B:
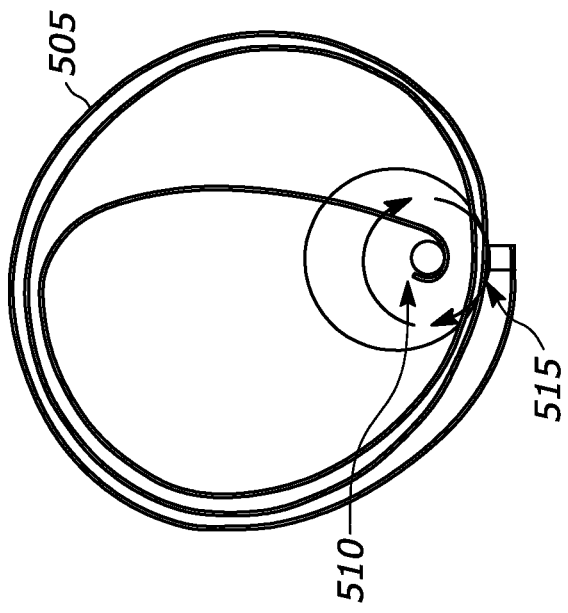
FIG. 5B is a cross-sectional view that depicts how rotation of a control rod of the expandable endotracheal tube causes corresponding movement of the constant force spring in accordance with an illustrative embodiment.
Figure 5A:
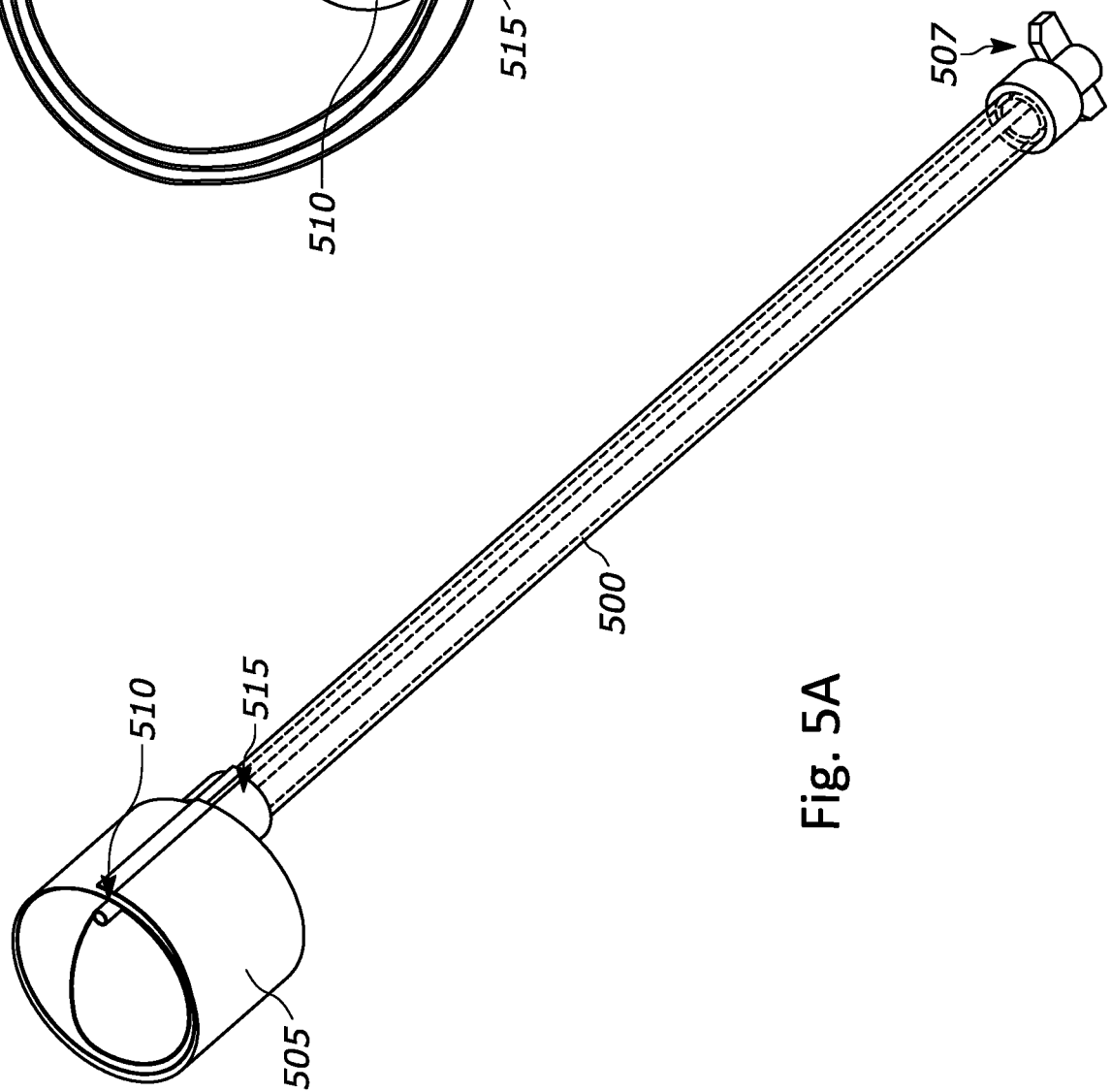
FIG. 5A depicts an expandable endotracheal tube 500 with a single constant force spring 505 in accordance with an illustrative embodiment.

FIG. 5A depicts an expandable endotracheal tube 500 with a single constant force spring 505 in accordance with an illustrative embodiment. In alternative embodiments, additional constant force springs may be used. The embodiment of FIG. 5A includes an alternative control system in which a handle 507 is mounted directly to the control rod 510 without use of a joint and angled rod. FIG. 5B is a cross-sectional view that depicts how rotation of a control rod 510 of the expandable endotracheal tube 500 causes corresponding movement of the constant force spring 505 in accordance with an illustrative embodiment. As shown, a first end of the constant force spring 505 is mounted to a fixed rod 515, which is mounted to the distal end of the shaft. A second end of the constant force spring 505 is mounted to the control rod 510. It can be seen that clockwise rotation of the control rod 510 causes the constant force spring 505 to wrap around the control rod 510, which results in compression of the spring. Similarly, counterclockwise rotation of the control rod 510 causes the constant force spring 505 to unwrap from the control rod 510, which results in expansion of the spring. In alternative embodiments, the directions of rotation to facilitate expansion and compression may be reversed such that clockwise rotation results in expansion and counterclockwise rotation results in compression.

FIGS. 6-13 depict an alternative embodiment of an expandable endotracheal tube that utilizes a track system and an expandable stent to facilitate compression and expansion. Specifically, FIG. 6A is a side view of an expandable endotracheal tube 600 in a compressed (or unexpanded) state in accordance with an illustrative embodiment. FIG. 6B is a close-up sectional view of an expandable segment 605 (including a helix 630 inside of a stent 635, inside of a cuff 640) of the expandable endotracheal tube 600 in the compressed state in accordance with an illustrative embodiment. FIG. 6C is a side view of the expandable endotracheal tube 600 in an expanded state in accordance with an illustrative embodiment. FIG. 6D is a close-up sectional view of the expandable segment 605 of the expandable endotracheal tube 600 in the expanded state in accordance with an illustrative embodiment.

The expandable endotracheal tube 600 includes a connector 610 (or tube nozzle) for attachment to a breathing circuit and ventilator. The connector 610 is mounted to the proximal end of a shaft (or tube) 615 of the expandable endotracheal tube 600. The proximal end of the expandable segment 605 is mounted to a distal end of the shaft 615. The distal end of the expandable segment 605 is mounted to a tube tip 620. In this embodiment, proximal refers to a direction that extends toward the connector 610 (i.e., toward the ventilator) and distal refers to a direction that extends toward the tube tip 620 (i.e., toward the patient when the tube is in use).

A track 625 is mounted to the shaft 615 and to the connector 610. The track 625 is used to control expansion and compression of the expandable segment 605. The expandable segment 605 of the expandable endotracheal tube 600 includes an expandable helix 630 that is connected to the track 625. As a result, lateral movement of the track 625 causes lateral movement of the expandable helix 630. Specifically, movement of the track 625 in the distal direction causes the expandable helix 630 to expand, and movement of the track 625 in the proximal direction causes the expandable helix to compress. This relationship is depicted in FIG. 6. Specifically, FIG. 6A (compressed state) shows that more of the track 625 is sticking out from the connector 610 than in FIG. 6C (expanded state). Manipulation of the expandable helix 630 is described in more detail below.

The expandable segment 605 also includes a stent 635 mounted around the outside of the expandable helix 630. Thus, the stent 635 expands and compresses as the expandable helix 630 expands and compresses. A cuff 640 is mounted around an outer surface of the stent 635. The cuff 640 extends between a distal end of the shaft 615 and a proximal end of the tube tip 620. Similar to the stent 635, the cuff 640 also expands and compresses along with the expandable helix 630. The individual components of the expandable endotracheal tube 600 are described in more detail with reference to FIGS. 7-13.

Figure 7E:
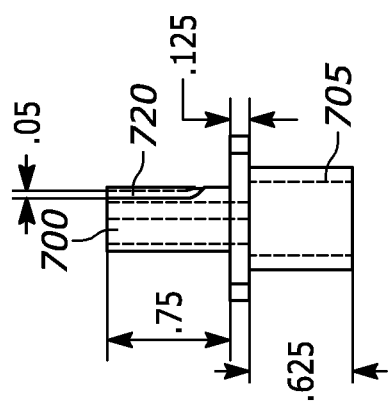
FIG. 7E is a cross-sectional side view of the connector in accordance with an illustrative embodiment.
Figure 7D:
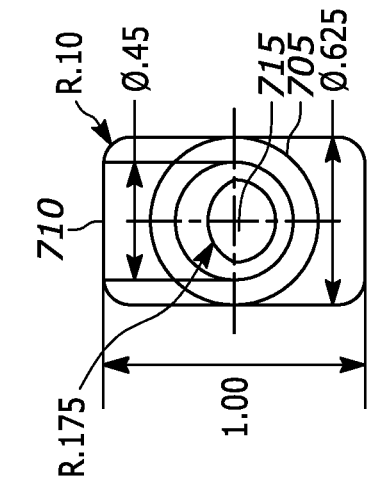
FIG. 7D is a plan view of a proximal end of the connector in accordance with an illustrative embodiment.
Figure 7B:
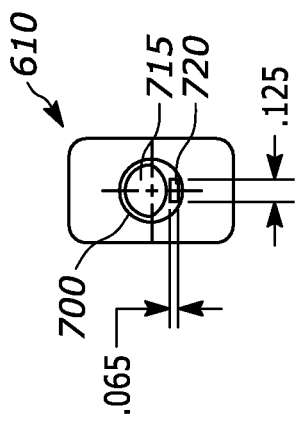
FIG. 7B is a plan view of a distal end of the connector in accordance with an illustrative embodiment.
Figure 7A:
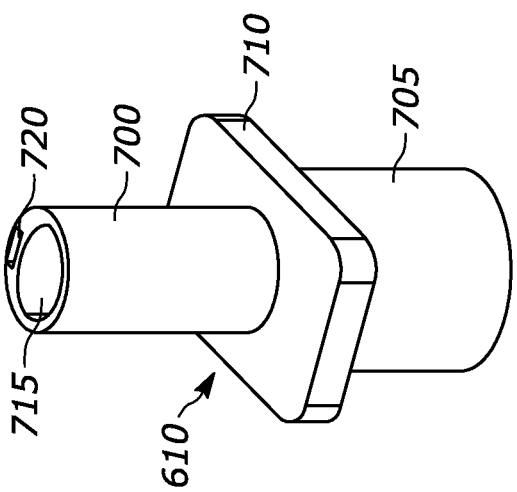
FIG. 7A is a perspective view of the connector in accordance with an illustrative embodiment.
Figure 7C:
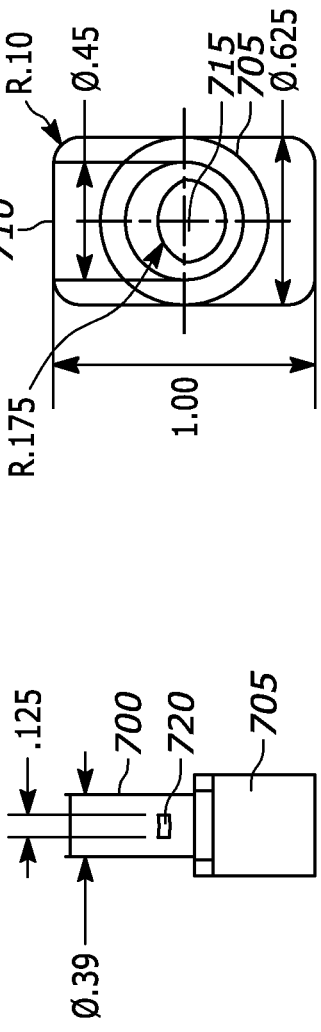
FIG. 7C is a bottom view of the connector in accordance with an illustrative embodiment.

FIG. 7A is a perspective view of the connector 610 in accordance with an illustrative embodiment. FIG. 7B is a plan view of the distal end 700 of the connector 610 in accordance with an illustrative embodiment. FIG. 7C is a bottom view of the connector 610 in accordance with an illustrative embodiment. FIG. 7D is a plan view of the proximal end 705 of the connector 610 in accordance with an illustrative embodiment. FIG. 7E is a cross-sectional side view of the connector 610 in accordance with an illustrative embodiment. It is noted that FIG. 7 includes various example dimensions (in inches) of the connector 610. These dimensions can be used with any of the embodiments described herein. However, it is to be understood that these dimensions are merely examples, and that other dimensions (or sizes) may be used in alternative embodiments.

In an illustrative embodiment, the connector 610 is made from polyethylene. Alternatively, a different material may be used. The connector 610 includes a stopper 710, which acts as a divider between the distal end 700 and the proximal end 705. When the connector 610 is mounted to the shaft 615, the distal side of the stopper 710 contacts the proximal end of the shaft 615 and determines how far the distal end 700 of the connector 610 extends into the shaft 715. In one embodiment, the distal end 700 of the connector 610 mounts within an interior of the shaft 615. The connector 610 can be secured to the shaft 615 via a friction fit, via an adhesive, and/or by any other method. The proximal end 705 of the connector 610 can be a universal attachment that allows the connector 610 to mount to a standard breathing circuit and ventilator, as known in the art.

The connector 610 includes a connector airway 715 that runs through the proximal end 705 of the connector 610, through the stopper 710, and through the distal end 700 of the connector 610. The connector airway 715 is aligned with an airway of the shaft 615 and is designed to receive air or oxygen from the ventilator. The connector 610 also includes a connector slot 720 that is sized to receive the track 625 depicted in FIG. 6. As shown, the connector slot 720 is formed in a sidewall of the distal end 700 of the connector 610. This sidewall has varying thickness (i.e., the bottom portion of the sidewall is thicker) to accommodate the connector slot 720. As best shown in the cross-sectional view of FIG. 7E, the connector slot 720 extends from the bottom side of the distal end 700 of the connector 610 and out through the distal end 700 such that the connector slot 720 extends into the shaft 615. As a result, the connector slot 720 is formed at an angle within the distal end 700 of the connector 610, and the track 625 protrudes from the bottom side of the connector 610 at an exit angle, as shown in FIGS. 6A and 6C. The exit angle can be 90° in one embodiment. Alternatively, a different angle can be used, such as 70°, 80°, 100°, 110°, 120°, etc. In an illustrative embodiment, the connector slot 720 of the connector 610 does not extend into the proximal end 705 of the connector 610 (i.e., the connector slot 720 is entirely incorporated into the distal end 700).

Figure 8A:
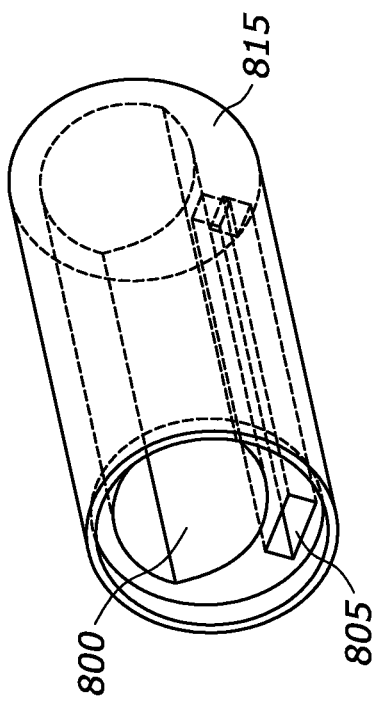
FIG. 8A is a partially transparent perspective view of the shaft in accordance with an illustrative embodiment.
Figure 8C:
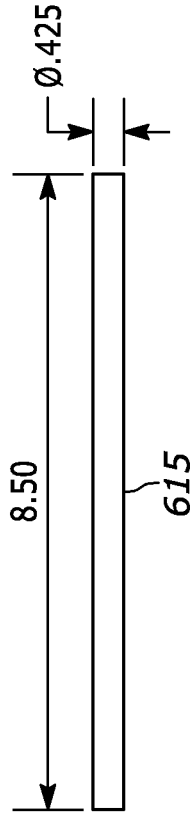
FIG. 8C is a side view of the shaft in accordance with an illustrative embodiment.
Figure 8B:
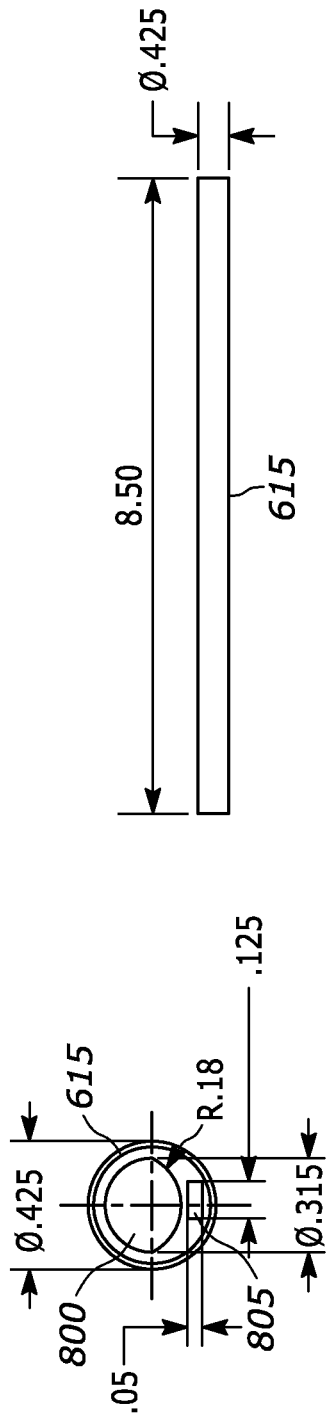
FIG. 8B is an end view of the shaft in accordance with an illustrative embodiment.

As discussed above, the connector 610 mounts to a proximal end of the shaft 615. FIG. 8A is a partially transparent perspective view of the shaft 615 in accordance with an illustrative embodiment. FIG. 8B is an end view of the shaft 615 in accordance with an illustrative embodiment. FIG. 8C is a side view of the shaft 615 in accordance with an illustrative embodiment. In one embodiment, the shaft 615 can be made from Tygon. Alternatively, a different biocompatible material can be used. It is noted that FIG. 8 includes various example dimensions (in inches) of the shaft 615. It is to be understood that these dimensions are merely examples, and that other dimensions (or sizes) may be used in alternative embodiments.

The shaft 615 includes a shaft airway 800 that extends along the entire length of the shaft 615. The shaft airway 800 is aligned with the connector airway 715 of the connector 610 when the connector is mounted to the shaft 615. This alignment enables air to freely flow through the entire length of the expandable endotracheal tube. The shaft 615 also includes a shaft slot 805 that aligns with the connector slot 720 when the connector 610 is mounted to the shaft 615. As shown, the shaft slot 805 is formed in a sidewall of the shaft 615. This sidewall has varying thickness (i.e., the bottom portion of the sidewall is thicker) to accommodate the shaft slot 805. In one embodiment, the shaft slot 805 can be tapered such that the distal end of the shaft slot 805 is narrower than its proximal end. Such a configuration allows enough room near the proximal end of the shaft for mated serrated edges of the track 625 and the expandable helix 630 to engage/disengage to/from one another within the shaft slot 805 such that the track 165 can be mounted or removed. In an illustrative embodiment, the shaft 615 can be made from a polymer. Alternatively, a different biocompatible material may be used.

Figure 9B:
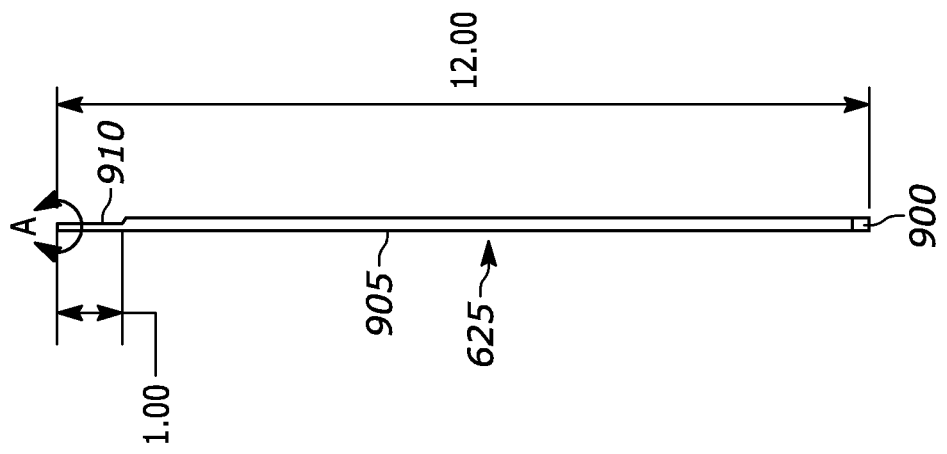
FIG. 9B is a plan view of the track in accordance with an illustrative embodiment.
Figure 9A:
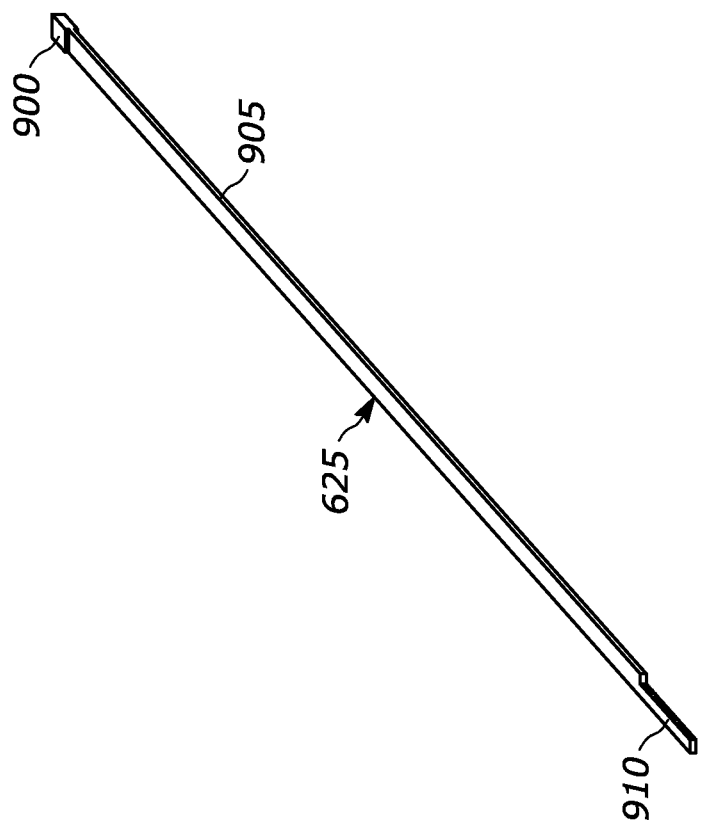
FIG. 9A is a perspective view of the track in accordance with an illustrative embodiment.
Figures 9C, 9D:
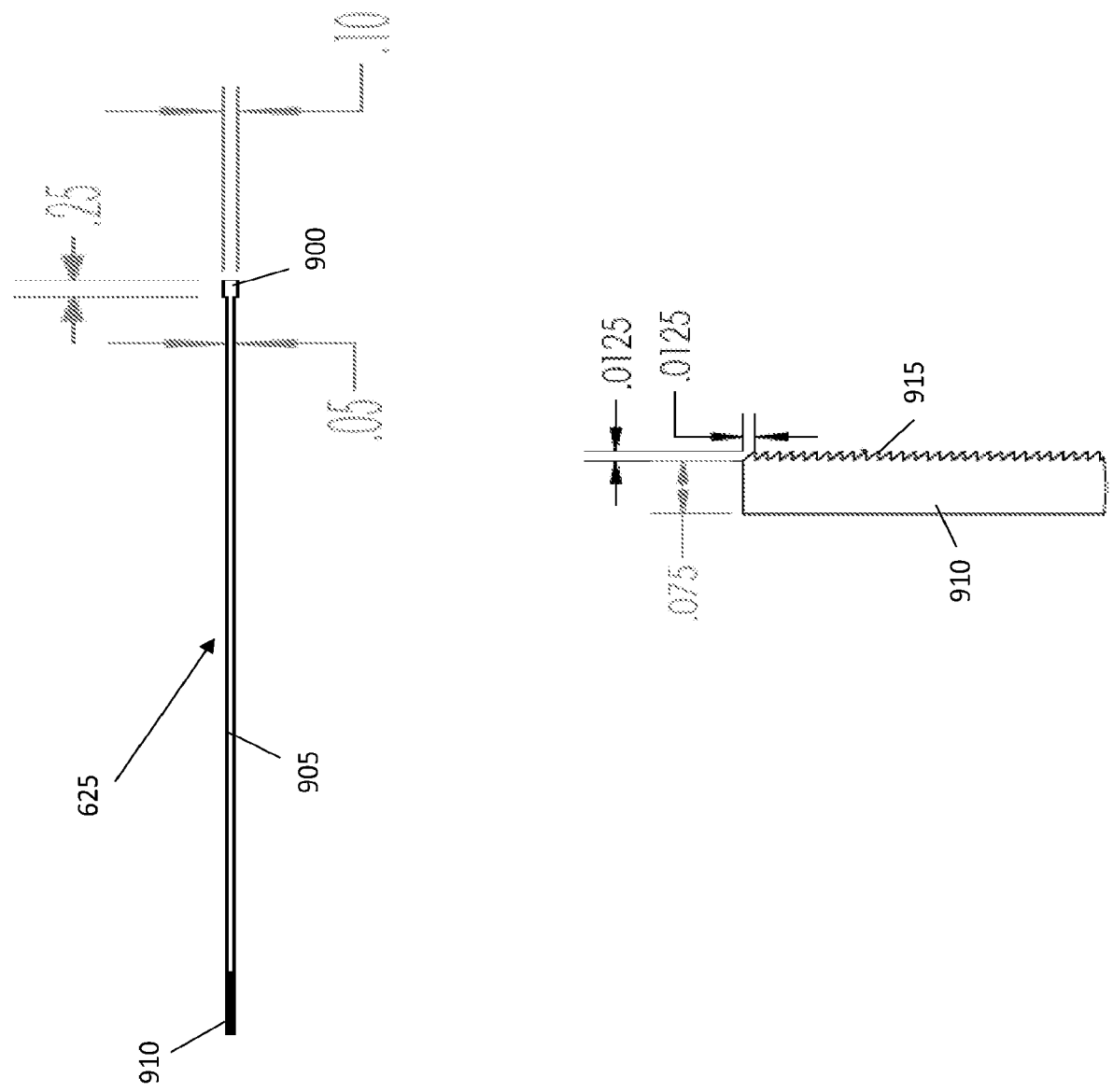
FIG. 9C is a side view of the track in accordance with an illustrative embodiment.
FIG. 9D is a sectional view of a distal end of the track in accordance with an illustrative embodiment.

FIG. 9A is a perspective view of the track 625 in accordance with an illustrative embodiment. FIG. 9B is a plan view of the track 625 in accordance with an illustrative embodiment. FIG. 9C is a side view of the track 625 in accordance with an illustrative embodiment. FIG. 9D is a sectional view of a distal end 910 of the track 625 in accordance with an illustrative embodiment. In an illustrative embodiment, the track 625 is made from nylon. Alternatively, other biocompatible materials may be used. It is noted that FIG. 9 includes various example dimensions (in inches) of the track 625. It is to be understood that these dimensions are merely examples, and that other dimensions (or sizes) may be used in alternative embodiments.

A body 905 of the track 625 is sized to fit within the connector slot 720 of the connector 610 and the shaft slot 805 of the shaft 615. A distal end 910 of the track 625 includes a serrated edge 915 that mates with a corresponding serrated edge on the expandable helix 630. As a result, the expandable helix 630 moves in lockstep with the track 625. As shown, the distal end 910 has a smaller width as compared to the body 905 of the track 625. This smaller width enables the track 625 to mate with the expandable helix 630 and still fit within the connector slot 720 of the connector 610 and the shaft slot 805 of the shaft 615.

The proximal end 900 of the track 625 is formed as a track connector that is designed to engage a control unit which manipulates the track 625. The control unit can be mounted to the expandable endotracheal tube 600 or it can be separate therefrom, depending on the embodiment. The control unit can be a graduated locking system that includes a built-in trigger. Each time the trigger is activated, the track 625 is moved forward (i.e., in the distal direction) and locked into position, which causes the expandable helix 630 to also move in the distal direction within the connector slot 720 and the shaft slot 805. As the expandable helix 630 moves distally, it expands and causes the entire expandable segment 605 to expand. Thus, the amount of expansion can be precisely controlled and maintained at a desired diameter by a user of the proposed tube. In one embodiment, the distance that the track 625 moves in response to a trigger activation can be ~0.0125 inches. Alternatively, a different distance may be used.

To compress the expandable portion 605 during extubation, the graduated locking system is disengaged. In one embodiment, disengaging the locking system reverses the direction that the track 625 travels upon activation of the trigger. In such an embodiment, the user can repeatedly activate the trigger until the expandable portion 605 is compressed. Alternatively, disengaging the locking system can cause the track 625 to move freely within the slots, which allows the track 625 to be easily retracted by the user. As a result, the track 625 can readily be moved and the expansion mechanism collapsed to its original state for extubation. In an illustrative embodiment, the track 625 is at least semi-flexible so that it is able to conform to the exit angle of the connector 610, as shown in FIG. 6A.

Figure 10B:
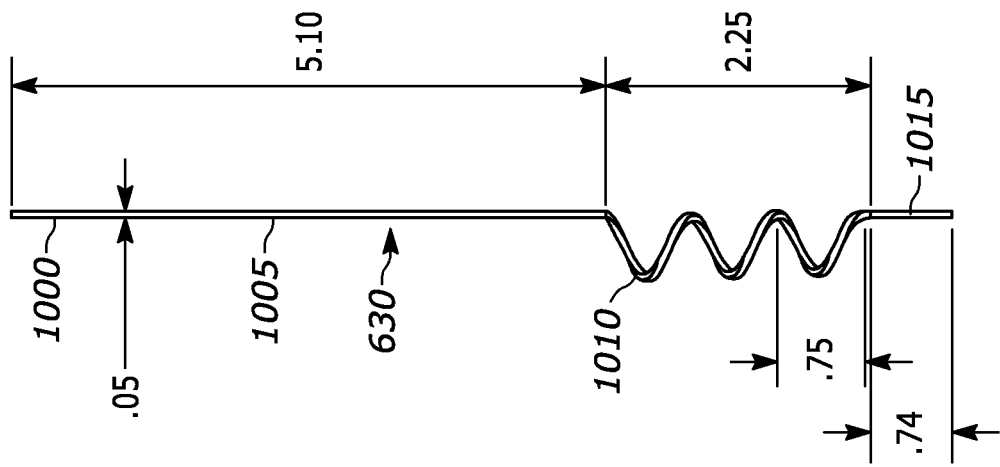
FIG. 10B is a side view of the expandable helix in accordance with an illustrative embodiment.
Figure 10A:
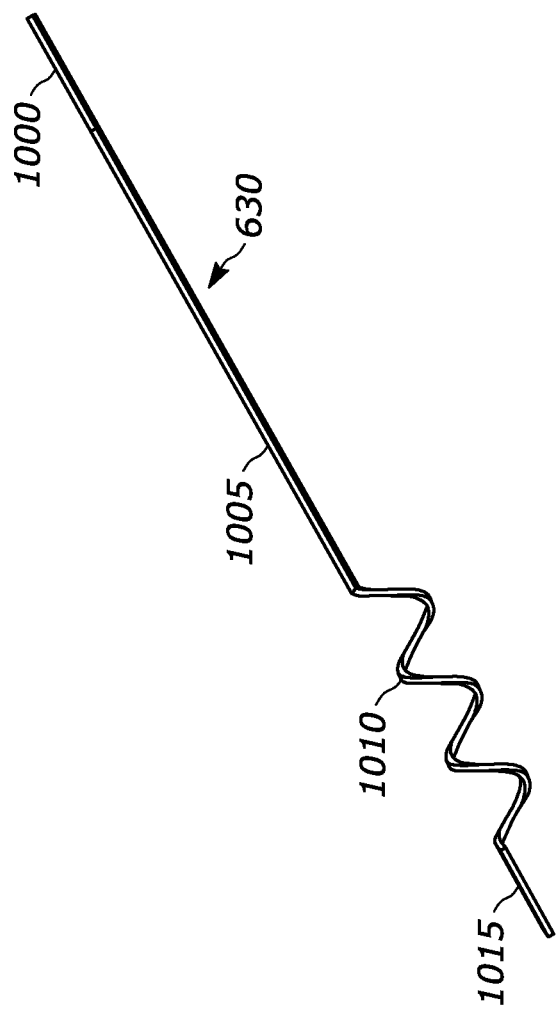
FIG. 10A is a perspective view of the expandable helix in accordance with an illustrative embodiment.

FIG. 10A is a perspective view of the expandable helix 630 in accordance with an illustrative embodiment. FIG. 10B is a side view of the expandable helix in accordance with an illustrative embodiment. FIG. 10C is a sectional view of a proximal end 1000 of the expandable helix 630 in accordance with an illustrative embodiment. FIG. 10 includes various example dimensions (in inches) of the expandable helix 630. It is to be understood that these dimensions are merely examples, and that other dimensions (or sizes) may be used in alternative embodiments.

The expandable helix 630 can be made from nylon and/or steel in one embodiment. Alternatively, a different material may be used. The expandable helix 630 includes the proximal end 1000, a body 1005 connected to the proximal end 1000, a helix 1010 (or helix portion) connected to the body 1005, and the distal end 1015 that is mounted within the tube such that it is stationary. In an illustrative embodiment, the distal end 1015 is anchored to the tube tip 620 using a fastener, clip, adhesive, or other technique. In another illustrative embodiment, the body 1005 of the expandable helix 630 can have a square profile having a side length of ~0.05 inches. Alternatively, a different shape of profile (e.g., circular, rectangular, triangular, etc.) and/or a different size may be used for the profile of the body 1005 of the expandable helix 630.

The proximal end 1000 of the expandable helix 630 includes a serrated edge 1020 that is designed to mate with the serrated edge 915 formed on the distal end 910 of the track 625. As discussed, this mating causes the expandable helix 630 to move in unison with the track 625. Because the distal end 1015 of the expandable helix 630 is anchored (i.e., stationary), movement of the proximal end 1000 in the distal direction causes the helix 1010 to expand in diameter. As shown, at least a portion of the helix 630 fits within the stent 635, which in turn fits within the cuff 640. In an alternative embodiment, instead of serrated edges, the expandable helix 630 and the track 625 can include other mating components, such as offset square wave patterns, etc. In another alternative embodiment, the track 625 can be integrally attached to the expandable helix 630.

Figure 11A:
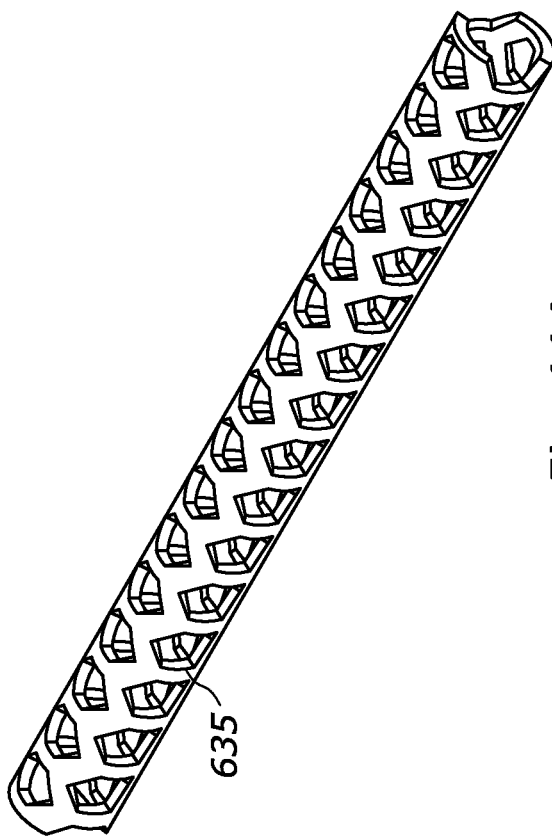
FIG. 11A is a perspective view of the stent in a compressed state in accordance with an illustrative embodiment.
Figure 11C:
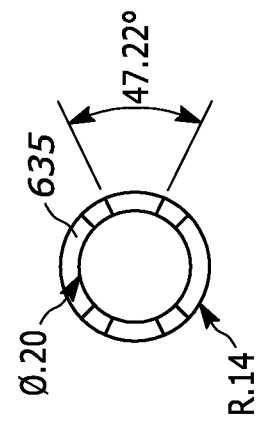
FIG. 11C is an end view of the stent in a compressed state in accordance with an illustrative embodiment.
Figure 11B:
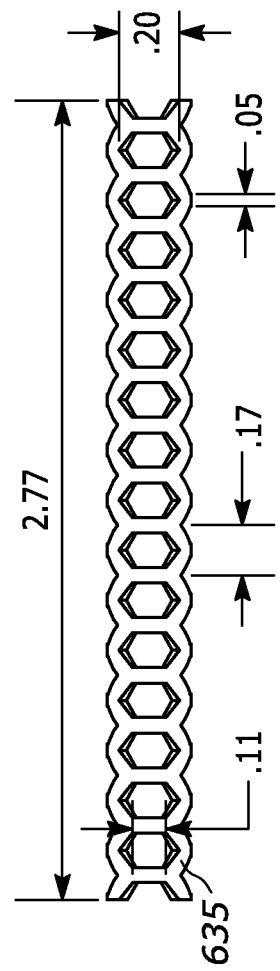
FIG. 11B is a side view of the stent in a compressed state in accordance with an illustrative embodiment.

FIG. 11A is a perspective view of the stent 635 in a compressed state in accordance with an illustrative embodiment. FIG. 11B is a side view of the stent 635 in a compressed state in accordance with an illustrative embodiment. FIG. 11C is an end view of the stent 635 in a compressed state in accordance with an illustrative embodiment. The dimensions used in FIG. 11 are merely examples, and other dimensions (or sizes) may be used in alternative embodiments.

In an illustrative embodiment, the stent 635 can be formed as an expandable steel mesh. However, any type of expandable stent known in the art may be used. In another illustrative embodiment, the proximal end of the stent 635 can be anchored within the distal end of the shaft 615 and the distal end of the stent 635 can be anchored within the proximal end of the tube tip 620. As such, during expansion, the ends of the stent 635 remain stationary. The ends of the stent can be anchored via friction fit, adhesive, a clip, a connector, or any other method.

Figure 12A:
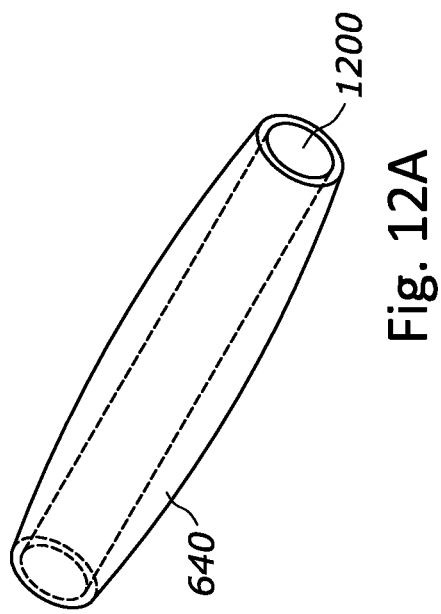
FIG. 12A is a perspective view of the cuff in accordance with an illustrative embodiment.
Figure 12C:
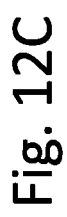
FIG. 12C is an end view of the cuff in accordance with an illustrative embodiment.
Figure 12B:
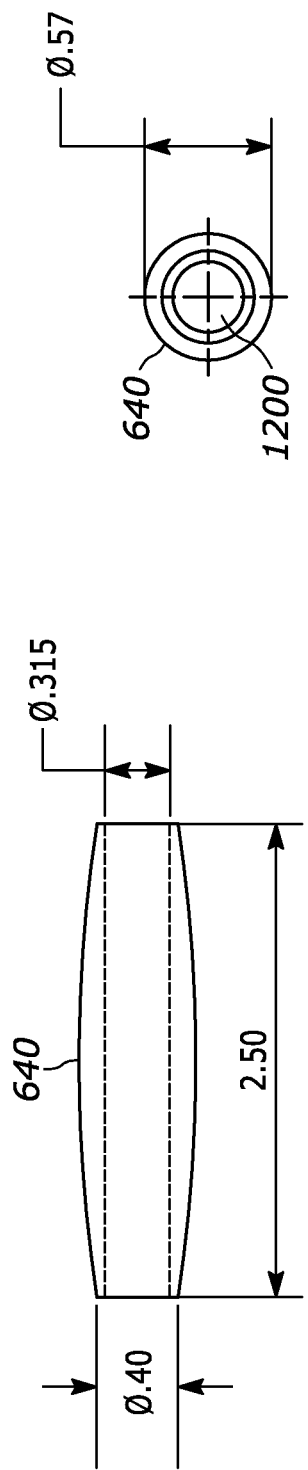
FIG. 12B is a side view of the cuff in accordance with an illustrative embodiment.

FIG. 12A is a perspective view of the cuff 640 in accordance with an illustrative embodiment. FIG. 12B is a side view of the cuff 640 in accordance with an illustrative embodiment. FIG. 12C is an end view of the cuff 640 in accordance with an illustrative embodiment. Similar to the other figures, the dimensions used in FIG. 12 are merely examples, and other dimensions (or sizes) may be used in alternative embodiments.

As shown in FIG. 6, the cuff 640 (or expandable cuff) wraps around and adheres to the outer surface of both the shaft 615 and the tube tip 620. The adherence can be achieved using a friction fit, an adhesive, or other technique. The cuff 640 includes a passageway 1200 that is sized to receive the stent 635. Air from the ventilator also flows through the passageway 1200 and into the tube tip 620. In an illustrative embodiment, the cuff 640 can be made from nitrile rubber. Alternatively, a different biocompatible material may be used, such as a polymer. The cuff 640 essentially replaces the balloon used in traditional endotracheal tubes. As depicted in FIG. 12, the cuff 640 is in a resting, compressed state.

On expansion of the expandable segment 605, the cuff 640 comes into contact with the trachea of the patient to prevent any leakage around the artificial airway. In an illustrative embodiment, the expandable segment 605 is expanded to the point of maximal contact with the trachea by forming itself around the cartilaginous rings within the trachea. However, this maximal contact does not result in excessive pressure against the trachea. Due to the significant surface area contact that the cuff 640 provides, the amount of pressure on the tracheal mucosa is reduced as compared to traditional endotracheal tubes. Additionally, testing has confirmed that the maximum pressure allowed to be created by the proposed tube is below the threshold known to be safe. This maximum pressure is dictated by the size and type of materials used for the proposed tube. For example, the stiffness of the expandable helix 630 and/or the malleability of the cuff 640 can be varied to vary the maximum pressure that can be exhibited by the expandable segment 605 in the expanded state. Additionally, when the expandable helix 630 is at its maximum diameter, the stent 635 is also necessarily at its maximum diameter for that configuration. It is noted that the cuff 640 is the only portion of the expansion segment 605 that comes into direct contact with the patient.

FIG. 13A is a perspective view of the tube tip 620 in accordance with an illustrative embodiment. FIG. 13B is a side view of the tube tip 620 in accordance with an illustrative embodiment. FIG. 13C is an end view of the tube tip 620 in accordance with an illustrative embodiment. Similar to the other figures, the dimensions used in FIG. 13 are merely examples, and other dimensions (or sizes) may be used in alternative embodiments.

The tube tip 620 includes a passageway 1300 that is sized to receive the stent 635. Air from the ventilator also flows through the passageway 1300, out the end of the tube tip 620, and into the patient. Specifically, the tube tip 620 includes a first opening 1305 and a second opening 1310 through which air from the ventilator leaves the tube tip 620 and enters the patient. The first opening 1305 is positioned at the distal end of the tube tip 620, which is tapered at an angle to facilitate insertion into the airway of the patient. The second opening 1310 is positioned in a sidewall of the tube tip 620, and is used as a vent to further assist with advancement of the tube into the airway of the patient. In an illustrative embodiment, the tube tip 620 can be made from a stiff material such that it acts as a stylet during intubation. For example, the tube tip 620 may be formed from a stiff polymer such as polyethylene or high-density polyethylene (HDPE). Alternatively, a different biocompatible material may be used. In some embodiments, the tube tip 620 can also be slightly curved in an anterior direction.

In one embodiment, the proposed expandable endotracheal tube can also include one or more temperature sensors and/or one or more carbon dioxide ($CO_2$) sensors mounted thereto. The one or more temperature sensors are used to monitor an internal temperature of the patient. The one or more carbon dioxide sensors are used to identify $CO_2$ exhaled by the patient to help ensure that the tube is initially placed in the trachea and not in the esophagus. Additionally, this sensor can be used to monitor both inhaled ($FiCO_2$) and exhaled ($ETCO_2$) $CO_2$ currently managed by additional monitors in the OR and ICUs. The sensor(s) can be mounted within the expandable endotracheal tube (e.g., within the shaft 615, the expandable segment 605, and/or the tube tip 620). Alternatively, the sensor(s) can be mounted on an outer surface of the shaft 615, the expandable segment 605, and/or the tube tip 620. Data sensed by the sensor(s) can be transmitted to a computing device (e.g., smartphone, tablet, laptop, etc.) via wired or wireless communication, and a user can monitor the data through the computing device.

Thus, described herein is are expandable endotracheal tubes that increase the efficiency of endotracheal intubation while decreasing waste created by ancillary material needs (i.e., multiple sizes of tubes, syringes, and stylets), stock expiration prior to use, and multiple tube preparations. The proposed tubes also decrease the frequency and severity of airway irritation due to the way in which the tube contacts the tracheal tissue.

It is to be understood that any of the operations/processes described herein may be performed at least in part by a computing system that includes a processor, memory, transceiver, user interface, etc. The described operations/processes can be implemented as computer-readable instructions stored on a computer-readable medium such as the computer system memory. Upon execution by the processor, the computer-readable instructions cause the computing system to perform the operations/processes described herein, such as operation of the control unit to manipulate the track such that the tube expands and compresses.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An expandable endotracheal tube comprising:
   a shaft comprising part of an airway; and
   an expandable segment mounted to a distal end of the shaft, wherein the expandable segment includes:
   an expandable membrane; and
   a constant force spring positioned within the expandable membrane at the distal end of the shaft such that the constant force spring forms a terminal end of the airway, wherein the constant force spring comprises a coiled strip of material, and wherein the constant force spring has a compressed configuration to allow for placement of the expandable endotracheal tube within a patient and an expanded configuration in which the expandable membrane is configured to form a seal with a trachea of the patient to enable positive pressure ventilation.

2. The expandable endotracheal tube of claim 1, further comprising an airway adapter mounted to a proximal end of the shaft, wherein the airway adapter connects to a ventilator.

3. The expandable endotracheal tube of claim 1, further comprising a control rod mounted to a first end of the constant force spring.

4. The expandable endotracheal tube of claim 3, further comprising a fixed rod mounted to the distal end of the shaft such that the fixed rod is stationary relative to the shaft.

5. The expandable endotracheal tube of claim 4, wherein a second end of the constant force spring is mounted to the fixed rod such that rotation of the control rod in a first direction results in expansion of the constant force spring and rotation of the control rod in a second direction results in compression of the constant force spring.

6. The expandable endotracheal tube of claim 1, further comprising a bougie mounted to the distal end of the shaft such that the bougie extends past a distal end of the expandable membrane.

7. The expandable endotracheal tube of claim 1, further comprising a sensor port formed in a body of the shaft, wherein the sensor port extends longitudinally along the shaft to provide access to the expandable segment.

8. The expandable endotracheal tube of claim 7, further comprising a sensor within the sensor port, wherein the sensor comprises a temperature sensor or a carbon dioxide sensor.

9. The expandable endotracheal tube of claim 7, wherein the constant force spring comprises a first constant force spring, and further comprising a second constant force spring positioned within the expandable membrane such that there is a gap between the first constant force spring and the second constant force spring.

10. The expandable endotracheal tube of claim 9, further comprising a groove in the expandable membrane, wherein the groove is positioned in the gap between the first constant force spring and the second constant force spring, and wherein the gap is sized to receive a cartilage ring in the airway of the patient.

11. A method of making an expandable endotracheal tube, the method comprising:
    forming a shaft that has a proximal end and a distal end, wherein the shaft has an airway that runs longitudinally within the shaft;
    mounting a fixed rod to a distal end of the shaft; and
    mounting an expandable segment to the distal end of the shaft, wherein mounting the expandable segment includes:
    mounting a constant force spring such that a first end of the constant force spring is mounted to the fixed rod, wherein the constant force spring has a compressed configuration to allow for placement of the expandable endotracheal tube within a patient and an expanded configuration in which the expandable segment forms a seal with a trachea of the patient to enable positive pressure ventilation; and
    mounting an expandable membrane to the shaft such that the expandable membrane surrounds the constant force spring.

12. The method of claim 11, wherein forming the shaft further comprises forming a control rod port within a body of the shaft, wherein the control rod port extends to the distal end of the shaft.

13. The method of claim 12, further comprising mounting a control rod within the control rod port such that the control rod rotates within the control rod port.

14. The method of claim 13, wherein mounting the constant force spring comprises mounting a second end of the constant force spring to the control rod such that rotation of the control rod in a first direction results in expansion of the constant force spring and rotation of the control rod in a second direction results in compression of the constant force spring.

15. The method of claim 11, wherein forming the shaft further comprises forming one or more sensor ports within a body of the shaft.

16. The method of claim 11, further comprising mounting a bougie to the distal end of the shaft such that the bougie extends past a distal end of the expandable segment.

\* \* \* \* \*